United States Patent (10) Patent No.: US 10,981,183 B2
Moser et al. (45) Date of Patent: Apr. 20, 2021

(54) HANDPIECE FOR SPRAYING ON A FLUID JET AND INSERTION MEMBER FOR THIS HANDPIECE

(71) Applicant: Medaxis AG, Baar (CH)

(72) Inventors: Beat Moser, Uerzlikon (CH); Beat Widmer, Lucerne (CH); Martin Butler, Hohenrain (CH); Roman Good, Zürich (CH); Cyrill Rothlin, Hunenberg (CH)

(73) Assignee: Medaxis AG, Baar (CH)

( * ) Notice: Subject to any disclaimer, the term of this patent is extended or adjusted under 35 U.S.C. 154(b) by 10 days.

(21) Appl. No.: 15/806,374

(22) Filed: Nov. 8, 2017

(65) Prior Publication Data

US 2018/0126392 A1 May 10, 2018

(30) Foreign Application Priority Data

Nov. 9, 2016 (EP) .................................... 16197862

(51) Int. Cl.
  *B05B 1/02* (2006.01)
  *A61B 17/3203* (2006.01)
  *B05B 15/40* (2018.01)
  *B05B 1/30* (2006.01)

(52) U.S. Cl.
  CPC ............ *B05B 1/02* (2013.01); *A61B 17/3203* (2013.01); *B05B 1/3013* (2013.01); *B05B 15/40* (2018.02)

(58) Field of Classification Search
  CPC ....... B05B 1/02; B05B 1/3013; B05B 7/1413; B05B 15/65–658; B05B 15/40; A61B 17/3203

USPC ................................. 239/154, 590–591, 600
See application file for complete search history.

(56) References Cited

U.S. PATENT DOCUMENTS

| 1,393,562 | A | | 10/1921 | Matthews |
| 2,395,479 | A | | 2/1946 | Heany |
| 3,032,277 | A | * | 5/1962 | Petty .................. B05B 15/40 239/408 |
| 3,705,693 | A | | 12/1972 | Franz |

(Continued)

FOREIGN PATENT DOCUMENTS

| DE | 4120613 A1 | 3/1992 |
| EP | 2251142 A1 | 11/2010 |

(Continued)

OTHER PUBLICATIONS

Japanese Ofifce Action, Appl. No. 2017-216685, dated Mar. 12, 2019.

(Continued)

*Primary Examiner* — Tuongminh N Pham
(74) *Attorney, Agent, or Firm* — Fishman Stewart PLLC

(57) ABSTRACT

The present invention relates to a handpiece for spraying on a fluid jet with a handpiece casing in which a nozzle element for forming the jet geometry of the fluid jet is accommodated. The present invention is based on the object of specifying a handpiece for spraying on a fluid jet which can be produced in a more simple and inexpensive manner, and proposes to satisfy the object in that a nozzle element be fixedly connected to an integrally formed nozzle holder which sealingly abuts against the outer circumferential surface of the nozzle element and is fixed relative to the handpiece casing.

14 Claims, 5 Drawing Sheets

(56) References Cited

U.S. PATENT DOCUMENTS

| | | | | |
|---|---|---|---|---|
| 4,074,858 | A * | 2/1978 | Burns | B05B 12/06 |
| | | | | 111/127 |
| 4,244,521 | A * | 1/1981 | Guse | B05B 1/10 |
| | | | | 175/424 |
| 4,588,131 | A * | 5/1986 | Yamamoto | B05B 7/0062 |
| | | | | 239/428.5 |
| 4,660,773 | A * | 4/1987 | O'Hanlon | B26F 3/004 |
| | | | | 175/423 |
| 9,027,967 | B2 | 5/2015 | Geser et al. | |
| 9,427,764 | B2 | 8/2016 | Duquet et al. | |
| 2004/0217203 | A1 * | 11/2004 | Walti | B05B 1/3426 |
| | | | | 239/492 |
| 2005/0045742 | A1 * | 3/2005 | Nakamura | B05B 15/40 |
| | | | | 239/333 |
| 2005/0194472 | A1 * | 9/2005 | Geser | B05B 15/18 |
| | | | | 239/602 |
| 2010/0154792 | A1 | 6/2010 | Geser et al. | |
| 2010/0280461 | A1 * | 11/2010 | Forstreuter | A61M 5/31515 |
| | | | | 604/228 |
| 2010/0286636 | A1 * | 11/2010 | Braendli | A61B 17/3203 |
| | | | | 604/310 |
| 2014/0128808 | A1 * | 5/2014 | Keitel | A61M 5/3287 |
| | | | | 604/117 |
| 2014/0161504 | A1 * | 6/2014 | Duquet | A45D 34/04 |
| | | | | 401/147 |
| 2015/0209936 | A1 | 7/2015 | Ihara et al. | |

FOREIGN PATENT DOCUMENTS

| | | |
|---|---|---|
| JP | S59-84581 A | 5/1984 |
| JP | S60-195008 A | 10/1985 |
| JP | 2001-315811 A | 11/2001 |
| JP | 2002-102856 A | 4/2002 |
| JP | 2002-536170 A | 10/2002 |
| JP | 2007-517646 A | 7/2007 |
| JP | 2014529486 A | 11/2014 |
| WO | 00/47330 A1 | 8/2000 |
| WO | 2015/124844 A1 | 8/2015 |

OTHER PUBLICATIONS

European Search Report, EP106287, dated Apr. 11, 2017.
English translation of Chinese Office Action, Appl. No. 201711097837.2, dated Sep. 27, 2019.

* cited by examiner

HANDPIECE FOR SPRAYING ON A FLUID JET AND INSERTION MEMBER FOR THIS HANDPIECE

CROSS-REFERENCE TO RELATED APPLICATIONS

This application claims priority to European Patent Application No. 16197862.2, filed Nov. 9, 2016, the contents of which are hereby incorporated by reference in its entirety.

TECHNICAL FIELD

The present invention relates to a handpiece for spraying on a fluid jet with a handpiece casing in which a nozzle element for forming the jet geometry of the fluid jet is accommodated.

BACKGROUND

Such a handpiece is known, for example, from EP 2 251 142 A1. The present invention relates in particular to a handpiece for spraying on a fluid jet in the context of debridement by use of a fluid jet. In this method, a microfluid jet is sprayed onto the wound surface of a wound of a living being, usually a human being, in order to remove tissue or secretion. A fluid jet is generally a treatment fluid which is formed, for example, predominantly or exclusively from water or a physiological saline solution. The fluid jet must fulfill special requirements. It must have a small beam diameter and extend in a coherent manner over a relatively long distance in order to impact as targeted or focused as possible onto the wound and at a predetermined jet pressure. The nozzle elements used for this purpose are accordingly very small. They have an outer diameter of typically no more than 4 mm. There are various possibilities of forming the nozzle element. EP 2 251 142 A1 discloses a nozzle block which is inserted into a recess of a cylindrical nozzle body. Disposed in an annular gap between the nozzle block and the nozzle body is an O-ring which is to seal the nozzle against the nozzle holder. On its outer circumferential surface, the nozzle holder also comprises several O-rings that are provided with an axial spacing, i.e. one behind the other in the direction of flow.

The known structure is complex. Moreover, it cannot provide a satisfactory solution for pressure of up to 150 bar acting when using debridement by way of a fluid jet. Furthermore, the assembly is complicated because the relatively small nozzle block must be manipulated and inserted into the recess of the nozzle body and be sealed therein.

SUMMARY

The present invention is based on the object of specifying a handpiece for spraying on a fluid jet which can be produced in a more simple and inexpensive manner. Furthermore, the present invention seeks to provide an insertion member for a handpiece which can be produced inexpensively. The insertion member is a subunit within the handpiece and, if necessary, can be used as a consumable part in a handpiece that is designed as a reusable part.

For solving the problem, a handpiece having the features disclosed herein is provided with the present invention. With the handpiece according to the invention, the nozzle element is fixedly connected to an integrally formed nozzle holder i.e. an unitary nozzle holder. This connection makes it possible to safely manipulate the relatively small nozzle element during assembly. The nozzle element of the handpiece according to the invention has a length of typically no more than 30 mm, preferably between 5 and 25 mm, and an outer diameter of typically no more than 1 mm. The inner diameter of the flow passage of the nozzle element, which is typically provided with a round cross-section, can be between 0.15 and 0.6 mm, preferably between 0.25 and 0.35 mm, particularly preferably at 0.3±0.05 mm.

The nozzle holder is preferably formed from plastic material and can accordingly be easily produced as a mass product. The nozzle holder furthermore abuts in a sealing manner against the outer circumferential surface of the nozzle element so that the nozzle holder not only permits improved manipulating during assembly but also at the same time effects the seal on the outer circumferential surface of the nozzle element, so that a separate seal can be dispensed with when sealing the outer circumferential surface against the flowing fluid or at least one of the face sides of the nozzle element, respectively. The fluid is typically discharged to the environment at the outlet side of the nozzle element. The acting liquid pressure, which, due to the outer circumferential seal of the nozzle element by the nozzle holder, can be applied against the nozzle element at the face side, is applied at the oppositely disposed inlet end without any concern arising that the fluid can escape at points other than through the flow channel formed within the nozzle element.

The outlet end of the nozzle element typically projects over the nozzle holder, whereas the inlet end of the nozzle element is accommodated within the nozzle holder, whereby the inlet to the nozzle element is formed and sealed by the nozzle holder, i.e. specifically the walls surrounding the inlet.

According to the present invention, the nozzle holder is defined relative to the handpiece i.e. fixed against the handpiece. This fixation can be effected directly by interaction between the handpiece and the nozzle holder or indirectly through further parts of a prefabricated insertion member whose core piece is the nozzle holder with the nozzle element, where all elements of the insertion member are typically firmly connected to one another, preferably adhesively bonded together. In such an embodiment, the handpiece typically only forms a casing which surrounds the components forming the fluid jet and, in a manner suitable for the purpose of application, forms a casing which satisfies the aesthetic, hygienic and also practical requirements and, in particular, can be held and manipulated securely by the user of the handpiece. The handpiece casing can be configured to have one or more components. It is typically shaped as an elongate handpiece casing and comprises an opening at its end on the outlet side which allows the fluid jet to exit, whereas the oppositely disposed end typically forms a tube inlet opening which transfers the tube with little play into the interior of the handpiece casing. With regard to the high pressures, the tube is typically a co-extruded tube, i.e. a multilayer tube in which an inner tube segment can be made of plastic material having high strength, for example polyamide, whereas an outer tube segment can be made of polyurethane. On the side facing away from the handpiece, the tube typically comprises a coupling element by way of which the handpiece with the tube can be connected to a pump. The coupling element can be, for example, a Luer coupling element.

The nozzle holder can be connected to the nozzle element in a force-fit and/or positive-fit manner. According to the invention, the nozzle holder is configured in one piece, i.e. as an integrally formed component or a unitary component, for example, by way of primary moldings, preferably by way of plastic injection molding. The nozzle element can be inserted into such a nozzle holder and, for example, adhesively bonded thereto. The nozzle element can have projections formed on its outer circumferential surface in order to reliably prevent the nozzle element from being pressed out from the nozzle holder due to the liquid pressure acting on the inlet side. For this purpose, for example, a collar projecting radially outwardly can be formed on the nozzle element, which collar interacts with an ring-shaped mating surface which is formed on the nozzle holder in order to axially lock the nozzle element. Such surfaces extending substantially radially can in a particular manner effect the seal between the nozzle element and the nozzle holder.

In view of a production as inexpensive and simple as possible, it is preferable to connect the nozzle holder to the nozzle element by overmolding the nozzle element. The connection between the nozzle holder and the nozzle element is there at least effected in a force-fit manner due to the plastic material solidifying against the outer circumferential surface of the nozzle element, typically curing subject to dwell pressure.

At least the insertion member, preferably the entire handpiece are intended as consumable parts, and it is therefore important for the present invention to manufacture the handpiece overall at low costs. For example, a nozzle element is typically used which is composed of a metallic pipe and one or more aperture plates welded thereonto at the end side. The pipe is there prepared as a semi-finished product and provided with a channel, the flow diameter of which is between 0.15 and 0.6 mm. The outer diameter of the pipe is typically no more than 1 mm. Such pipe can be produced inexpensively. The aperture plate preferably forms a nozzle channel with an inner diameter of between 0.03 and 0.2 mm. With regard to the preferred positive-fit connection between the nozzle holder and the nozzle element, the nozzle element comprises a surface contour on its outer circumferential surface. This surface contour can be obtained, for example, by roughening the initially smooth metal surface of the nozzle element. The roughening can be effected by blast treatment, for example, sandblasting. However, a surface contour which is applied selectively by laser engraving is preferred. In view of the desired axial fixation of the nozzle element, it is understood that a surface contour should have contours that run in particular in the circumferential direction. A groove circulating in the circumferential direction or similar circumferential contouring can be introduced into the initially smooth outer circumferential surface of the nozzle element by way of laser engraving the outer circumferential surface. In view of an inexpensive production with simultaneously a good seal and connection between the nozzle element and the nozzle holder, it has proven to be advantageous to provide between one and four such circumferential contourings distributed with axial spacing on the outer circumferential surface of the nozzle element.

In particular, when the nozzle element is overmolded with liquid plastic material, an improved connection and seal arises with any kind of surface contouring, since the plastic material, which has been melt-filled, penetrates into the radial projections or recesses on the outer circumferential surface of the nozzle element and cures there.

According to a preferred development of the present invention, a flow channel is disposed upstream of the inlet end of the nozzle element, where its diameter is greater than the diameter of the nozzle element and it is formed in the nozzle holder. This flow channel typically tapers in the direction of flow and is typically located between the nozzle element and the tube for supplying the fluid to be ejected. The flow channel formed in the nozzle holder can there be formed cylindrically directly adjoining the nozzle element and arise during the injection-molding of the nozzle holder as a molding of a core which abuts against the nozzle element at the face side, seals the latter and holds it in position for injection molding. The inlet end of the nozzle element is therefore located within the nozzle holder. The outlet end of the nozzle element projects over the latter while having a length corresponding at least to three time the diameter of the nozzle element, preferably five to ten times the diameter of the nozzle element, in order to ensure in particular that no plastic material escaping from the cavity forming the nozzle holder and along the outer circumferential surface of the nozzle element blocks the outlet end of the nozzle holder when the nozzle element is overmolded with plastic material. A longitudinal section of the nozzle element projecting over the nozzle holder is during overmolding also used for fixating and positioning the nozzle element with the objective of arranging the latter on the central longitudinal axis of the nozzle holder after the plastic material forming the nozzle holder has cured, so that the nozzle element is arranged coaxially relative to the tube once all the components of the handpiece have been joined.

In order to protect the nozzle element protruding in this manner over the nozzle holder, a nozzle cap is proposed according to a preferred development of the present invention which reaches over the nozzle holder on the outlet side. Accordingly, the nozzle cap is provided at least in the direction of flow downstream of the fluid to be delivered and thereby on the outlet side of the nozzle holder. The nozzle cap typically comprises a bore which accommodates the nozzle element only partially. The nozzle cap then preferably also overlaps the face side end of the nozzle element. Particularly preferably, the nozzle cap forms a flange region which projects radially inwardly over the outer circumferential surface of the nozzle element and typically forms an annular surface against which the face side of the nozzle element abuts. Due to this abutment, a further positive-fit abutment of the nozzle element arises after the nozzle cap and the nozzle holder have been joined, which also holds the nozzle element even when the connection between the nozzle holder and the nozzle element should fail due to the liquid pressure acting during treatment. A further locking mechanism is thus provided for preventing the nozzle element from being pressed out from the handpiece during treatment. The face side abutment of the flange region against face side of the nozzle element is typically effected within the framework of the assembly when the nozzle cap is pushed over the end on the outlet side of the nozzle element and is bonded to the nozzle holder, in particular adhesively bonded thereto. An axial pressure acting against the nozzle cap ensures that the annular surface formed by the nozzle cap abuts against the face side of the nozzle element generally without play.

In particular with regard to adhesively bonding the nozzle holder and the nozzle cap, it is preferable to form between the nozzle holder and the nozzle cap a free space which is preferably penetrated by the nozzle element and which is capable of receiving possibly overshooting adhesive and/or a seal element. Clearances between the nozzle holder and the nozzle cap and/or between an outer circumferential surface formed by the nozzle holder and an inner circumferential surface formed by the nozzle cap are preferably provided for this adhesive connection into which adhesive can enter and through which adhesive can flow in order to enable, for example, a good distribution of the adhesive with volumetric dosing at the joining surfaces of the nozzle holder and the nozzle cap of the liquid adhesive. Said free space then collects excess adhesive. It can also accommodate an O-ring which is press-fitted by placing the nozzle cap against the nozzle holder, and is thereby sealingly abutted thereagainst. The free space is preferably designed as an annular space and is defined on the outer circumference by a ring-shaped rim which is formed by the nozzle holder. This ring-shaped rim is typically located at the end side in a ring-shaped groove that is recessed in the nozzle cap and that is defined at the inner circumference by a centering collar of the nozzle cap which enters with little play into the free space. Due to this nozzle rim, the O-ring can be press-fitted within the free space. For introducing the adhesive joining the nozzle cap to the nozzle holder, the nozzle cap preferably comprises at the level of the free space at least one adhesive introduction opening reaching up to the nozzle holder.

The adhesive is typically one-component adhesive that is UV-curable. In view of this, the nozzle cap and the nozzle holder are typically formed from transparent material, in particular, transparent plastic material such as polycarbonate, so that UV radiation can be radiated from the outside onto the adhesive after the introduction of the adhesive.

A nozzle element holder, which is prepared in this manner and composed of the nozzle holder and the nozzle cap and which preferably comprises only the three components nozzle cap, nozzle holder and nozzle element, is preferably connected to the tube with the aid of an adapter element. The adapter element has a nozzle holder receptacle adapted to receive the nozzle holder and a tube well adapted to receive the tube. This receptacle and this well are generally provided concentrically to one another and are typically spaced apart by a flow channel which is formed by the adapter element and typically transitions flush to the flow channel formed by the nozzle holder. Located preferably between the nozzle holder and the tube, preferably between the nozzle holder and a ring-shaped abutment surface of the adapter element, is preferably a filter element which ensures that contaminants possibly entrained by the treatment fluid are retained and do not reach the nozzle element in order prevent the nozzle element from being blocked and/or to prevent respective contaminants from entering into the wound to be treated. Such a filter element can be connected, for example, to the adapter element by overmolding with plastic material or can be provided as an insertion member thereon.

The adapter element is also preferably made of plastic material, specifically light-transmissive plastic material. The arrangement of the filter element on an annular surface of the adapter element offers the possibility of fixating the filter element between two dies which are introduced as moving cores into the cavity forming the adapter element prior to the plastic material forming the adapter element being injected. The filter element is clamped in between these dies and is captively received in the adapter element in a simple manner after the plastic material has solidified. The die abutting against the filter element on the outlet side regularly forms the nozzle holder receptacle, whereas the die acting from the inlet side forms the tube well, and also regularly the flow passage, which is reduced in diameter in relation to the diameter of the tube well and is formed within the adapter element.

The nozzle holder and/or the tube are preferably adhesively bonded to the adapter element. For this purpose, the adapter element preferably comprises an adhesive introduction opening reaching up to the nozzle holder and/or an adhesive introduction opening reaching up to the tube. Preferably, all the introduction openings for adhesive according to the developments of the present invention extend in the radial direction. The adhesive is in principle added volumetrically, so that it is ensured that a predetermined quantity of adhesive is injected for joining the components. In order to prevent radially injected adhesive connecting the adapter element to the nozzle holder from blocking the flow path on the face side between the nozzle holder and the adapter and/or from penetrating into the filter element, the filter element is typically provided overlapping an annular surface of the adapter element against which the nozzle holder is pressed or abuts, respectively. Any adhesive penetrating into this region from the outer circumferential surface of the nozzle holder is accordingly stopped at the radially outer region of this annular surface because the relatively soft filter material of the filter element acts like a seal element which is clamped in between the adapter element and the nozzle holder. The adapter element can also be connected to the nozzle holder or the tube by overmolding the nozzle holder or the adapter element, respectively, and/or the tube with plastic material forming the adapter element or the nozzle holder.

The tube well also preferably terminates at an annular surface formed by the adapter element. This annular surface forms a stop for the tube inserted into the adapter element. The inner circumferential surface defining the annular surface and formed by the adapter element is tapered slightly conically towards the flow outlet so that the tube inserted into the tube well is easily radially press-fitted. This embodiment results in a seal which reliably prevents the adhesive introduced radially at the level of the tube from reaching the face side of the tube and impeding the flow path there.

Due to the adapted configuration of the flow channel formed in the adapter element and/or the flow channel formed in the nozzle holder, the flow channel is preferably tapered in the direction towards the inlet end of the nozzle element. The flow channel formed in the nozzle holder preferably has a conical section which transitions the larger outer diameter of the flow channel formed in the adapter element to become the reduced outer diameter of the flow channel formed in the nozzle holder in the flow direction directly upstream of the nozzle element.

Preferably, the parts of the handpiece determining a particular shape of the fluid jet are positioned radially relative to one another in a predetermined manner, such that a user manipulating the handpiece can reliably assume for a specific radial orientation of the handpiece that this radial orientation determines in a predetermined manner, for example, the orientation of a flat nozzle jet. For this purpose, the adapter element preferably comprises on its outer circumferential surface a positive-fit element which interacts with a positive-fit mating element provided on the handpiece and/or on the nozzle holder for the radial positioning of the adapter element. The positive-fit element and the positive-fit mating element are preferably formed by bars which extend in the radial direction on the inner circumferential or outer circumferential surface, respectively, and which engage in recesses corresponding thereto.

The insertion member for a handpiece, which is protected by the independent aspect of the present invention, comprises a nozzle element of the type described above and an integrally formed nozzle holder fixedly connected to the nozzle element, which sealingly abuts against the outer circumferential surface of the nozzle element. This insertion member can be produced inexpensively as a consumable part, in particular if the further developments discussed above with regard to the nozzle holder and the nozzle cap are realized. An insertion member produced in this manner is connected to the tube via the adapter element and can by itself form the handpiece and thus the handpiece casing or can be inserted into a separate handpiece casing adapted to the ergonomic requirements.

The present invention further provides a method for manufacturing a handpiece for applying a fluid jet. In this procedure, the nozzle element is first prepared as a separate component. For this purpose, a pipe is regularly connected to at least one aperture plate. The aperture plate is cut from thin sheet metal, preferably by way of laser cutting and provided with one aperture opening that determines the jet geometry, possibly also with several aperture openings. When cutting the aperture plate from a larger piece of sheet metal, the former is initially not completely removed from the sheet metal plate. Instead, radial webs remain in order to keep the aperture plate connected to the piece of sheet metal. When laser-welding the aperture plate against the metallic pipe, these webs are severed, so that the aperture plate is then associated solely with the pipe and connected to it. The nozzle element is connected to an integrally formed nozzle holder such that the nozzle holder abuts sealingly against the outer circumferential surface of the nozzle element. The nozzle holder is particularly preferably connected in a sealing manner to the nozzle element by way of overmolding. The manipulatable subunit of the handpiece thus produced is then to a nozzle cap in the manner described above connected, preferably adhesively bonded thereto, preferably with the interposition of an O-ring which is arranged between the nozzle cap and the nozzle holder and clamped in therebetween and is preferably penetrated by the nozzle element. The nozzle holder and the nozzle cap are preferably adhesively bonded together in order to form a nozzle element holder to be manipulated in and of itself. The nozzle element holder there unites the nozzle element, the nozzle cap and the nozzle holder, where the nozzle cap surrounds and protects the end of the nozzle element on the outlet side. Prepared in this manner, the nozzle element holder is inserted into an adapter element which is preferably formed by injection molding. The end of a tube on the outlet side is also inserted into the adapter element. The adapter element with the nozzle element holder, on the one hand, and the tube, on the other hand, are preferably bonded by volumetric addition of adhesive. The adhesive is preferably cured by way of UV radiation, for which purpose the nozzle element holder and/or the adapter element are preferably formed from plastic material transmissible to UV.

BRIEF DESCRIPTION OF THE DRAWINGS

Further details and advantages of the present invention shall become apparent from the following description of an embodiment in combination with the drawing, in which.

DETAILED DESCRIPTION

Figure 1:
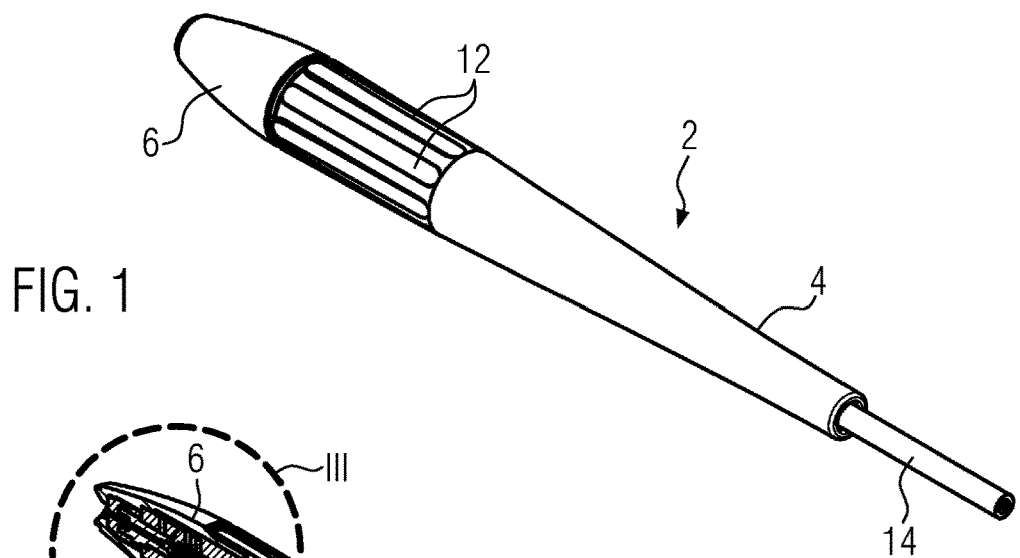
FIG. 1 shows a perspective side view of an embodiment of the front region of a handpiece.
Figure 2:
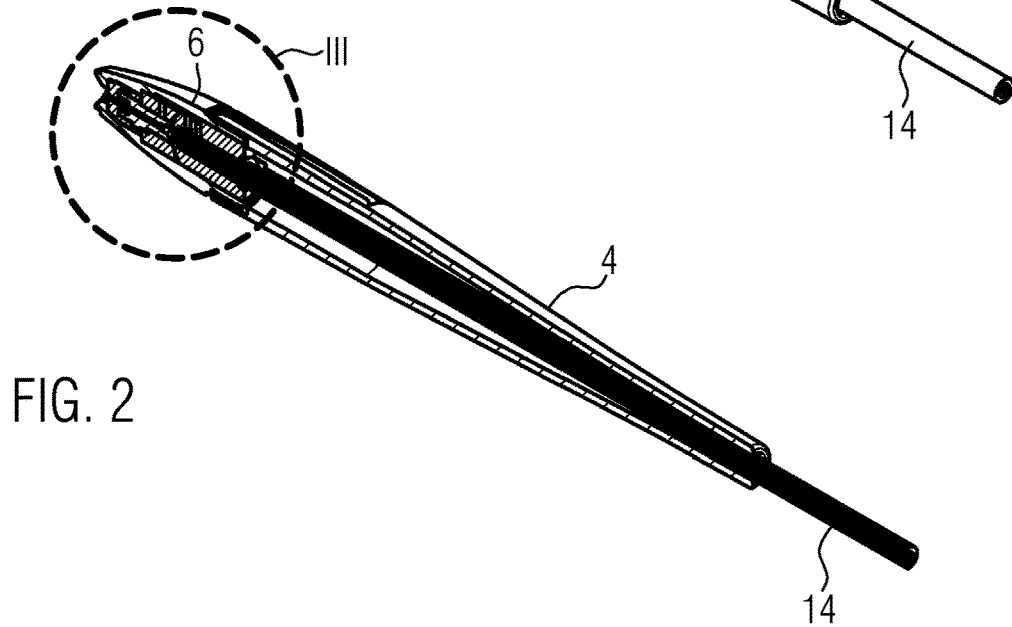
FIG. 2 shows a longitudinal sectional view of the embodiment shown in FIG. 1 in a perspective view.
Figure 3:
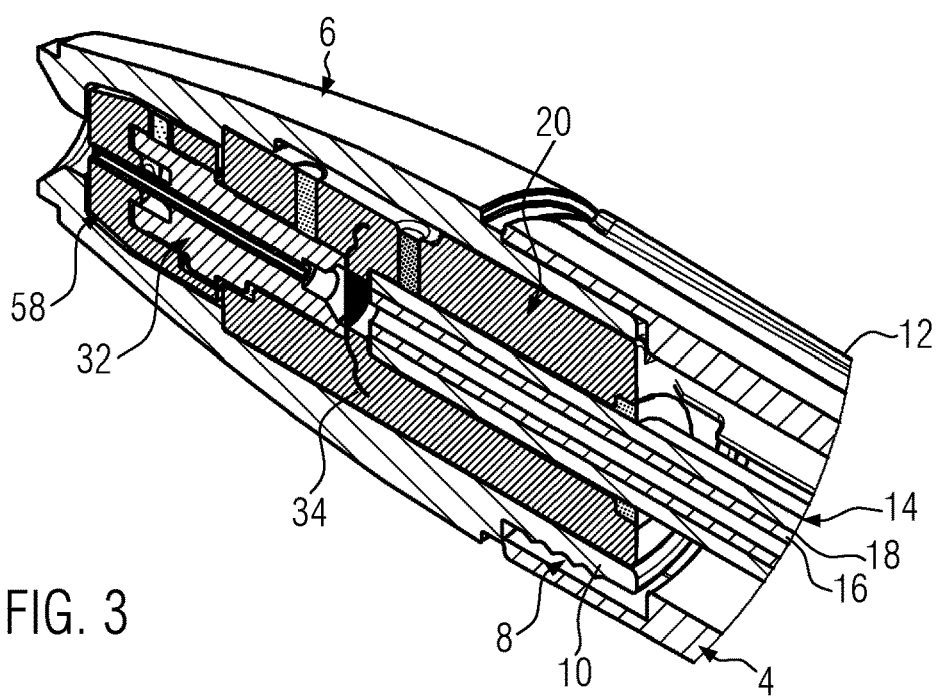
FIG. 3 shows detail III that is enlarged in FIG. 2.

In the drawing, reference numeral 2 denotes a handpiece casing with a handle shaft 4 and a casing cap 6 which are locked by way of a positive-fit connection denoted by reference numeral 8 in FIG. 3, for which purpose the casing cap 6 comprises a attachment nose 10 engaging the handle shaft 4, where the attachment nose is on its outer circumferential surface provided with ribs which interact with a configuration formed corresponding thereto on the inner circumferential surface of the handle shaft 4.

The handle shaft 4 comprises ribs 12, which extend axially on its front end on the outlet side and are provided on the outer circumferential surface, and which are provided distributed on the circumference and improve the haptic properties of the handle shaft 4. A user holding the handpiece casing 2 grips around the handpiece casing 2 with his hand. The rear end of the handpiece casing 2 on the inlet side rests in the hand of the user and is protruded by a tube 14 which is provided as a co-extruded tube with an inner tube section 16 made of polyamide and an outer tube section 18 made of polyurethane (see FIGS. 3, 4).

The tube 14 is received with its end on the outlet side in an adapter element 20, which for this purpose comprises a tube well 22 adapted for receiving the tube. The tube well 22 is substantially cylindrical and is adapted to the outer circumference of the tube 14 in such a way that adhesive can enter a gap between the tube 14 and the tube well 22. The end of the tube well 22 on the end of the flow outlet side is tapered radially inwardly in a conical manner so that the tube 14 is radially press-fitted at its end on the outlet side. With an axial spacing from an annular shoulder 23 formed by the adapter element 20, the adapter element 20 comprises an adhesive introduction opening 24 which reaches up to the tube 14 and is provided as a radial bore in the adapter element 20. Due to the tapering end of the tube well 22, adhesive applied therethrough can enter axially only as far as the end of the tube 14 on the outlet side, but not reach its face side. The adhesive introduced can fill the entire radial gap between the tube 14 and the tube well 22 in the axial direction For the purpose of verifying adequate adhesive bonding, an annular space 26 surrounding the tube 14 is recessed on the free face side of the adapter element 20 and is filled with adhesive 28 during bonding. The accumulation of adhesive 28 in this annular space 26 characterizes adequate filling of the annular gap with adhesive and thus reliable adhesive bonding of the tube 14 to the adapter element 20.

At the oppositely disposed end, the adapter element 20 forms a nozzle holder receptacle 30 which is configured to receive a nozzle holder marked with reference numeral 32. With the interposition of a filter element 34, this nozzle holder 32 abuts against a further annular shoulder 36 formed by the adapter element 20. Upstream of the filter element 34, the adapter element 20 forms a cylindrical flow channel 38 which terminates with the filter element 34 and transitions into a flow channel 40 which is recessed in the nozzle holder 32 and which has a cone section by way of which the diameter of the flow channel 38 is transitioned to a diameter of a cylindrical channel section 42 of the flow channel 40 which is provided in the flow direction directly upstream of a nozzle element 44. The nozzle element 44 is composed of a pipe member 46, to the end of which an aperture plate 48 is welded (cf. FIG. 6). The pipe member 46 and the aperture plate 48 are made of metal.

Figure 4:
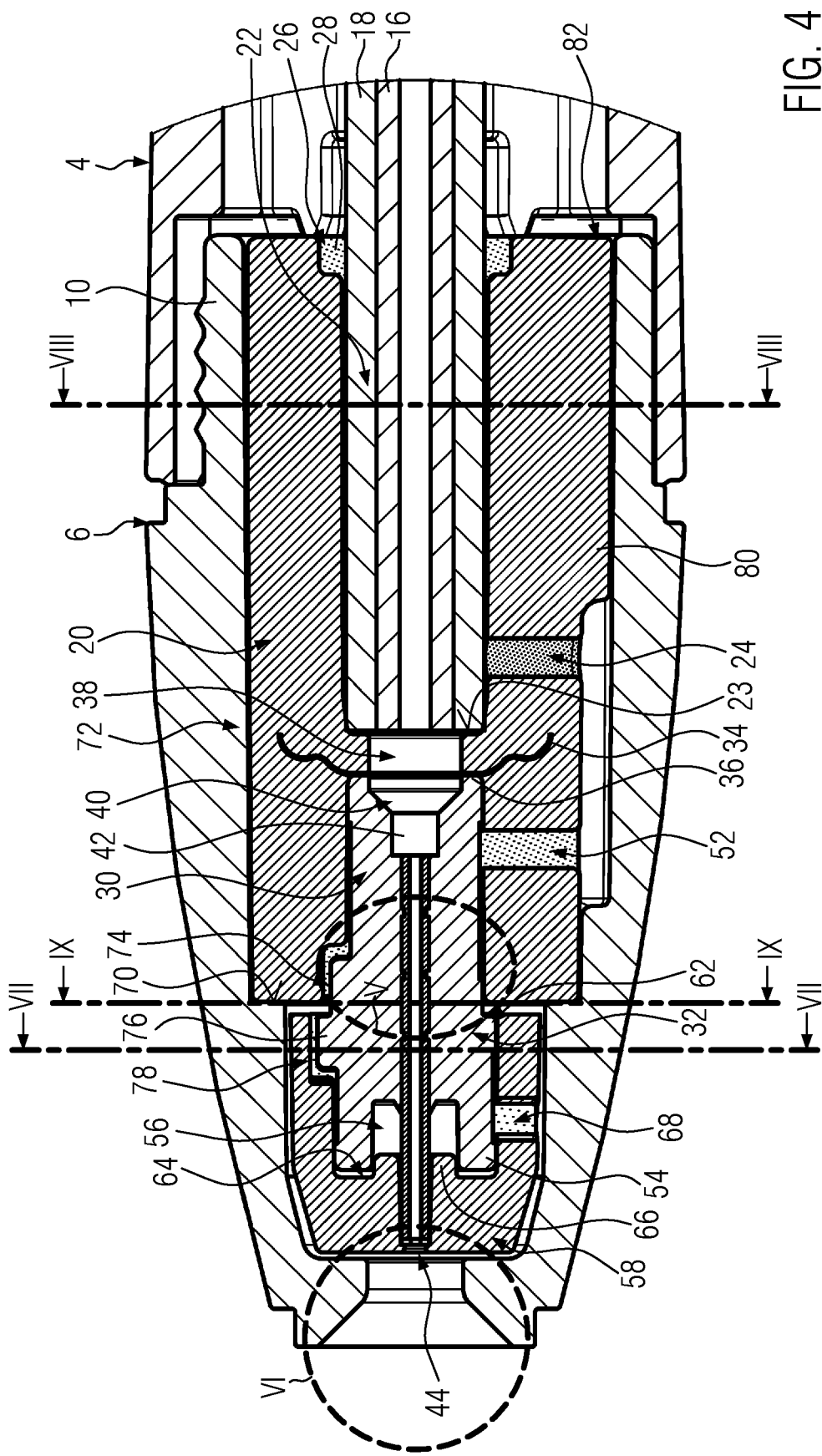
FIG. 4 shows the detail shown in FIG. 3 in a non-perspective longitudinal sectional view.
Figure 5:
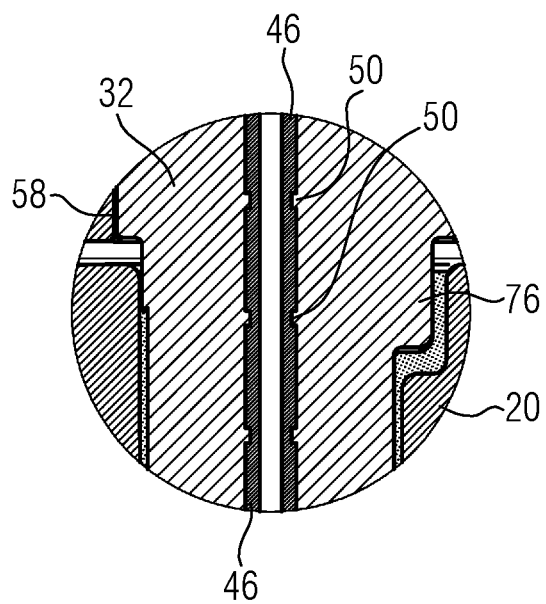
FIG. 5 shows detail V according to FIG. 4.

As illustrated by FIGS. 3 and 4, the inlet end of the nozzle element 44 is provided within the nozzle holder 32. The cylindrical channel section 42 has a larger diameter than the outer diameter of the nozzle element 44 so that the fluid delivered is applied with its pressure against the nozzle element 44 on the face side. The nozzle element 44 is connected in a fixed and fluidically tight manner to the nozzle holder 32, presently by overmolding the pipe member 46, which for this purpose has a surface contour on its outer circumferential surface, which is illustrated in FIG. 5. The pipe member 46 has several grooves 50 which are recessed in the circumferential direction on the outer circumferential surface by laser engraving, and in which the molten plastic material forming the nozzle holder 32 solidifies in order to establish a positive-fit connection between the nozzle element 44 and the nozzle holder 32. The connection between the nozzle holder 32 and the nozzle element 44 is also fluidically tight. The fluid applied subject to the system pressure in the cylindrical channel section 42 is discharged solely through the nozzle element 44 and sprayed onto a wound to be treated with a predetermined jet geometry by shaping in the aperture plate 48.

The adapter element 20 comprises a second adhesive introduction opening 52 which is recessed as a radial bore into the adapter element 20 and is provided with an axial spacing from the annular shoulder 36. This axial spacing corresponds approximately to the axial spacing of the adhesive introduction opening 24 from the annular shoulder 23. At its end on the outlet side, the nozzle holder 32 comprises a ring-shaped rim 54 which surrounds the nozzle element 44 circumferentially at a distance to the formation of a free space 56. This free space 56 is formed as an annular space and is defined at the outer circumference by the ring-shaped rim 54 and at the inner circumference by the outer circumferential surface of the nozzle element 44.

Figure 6:
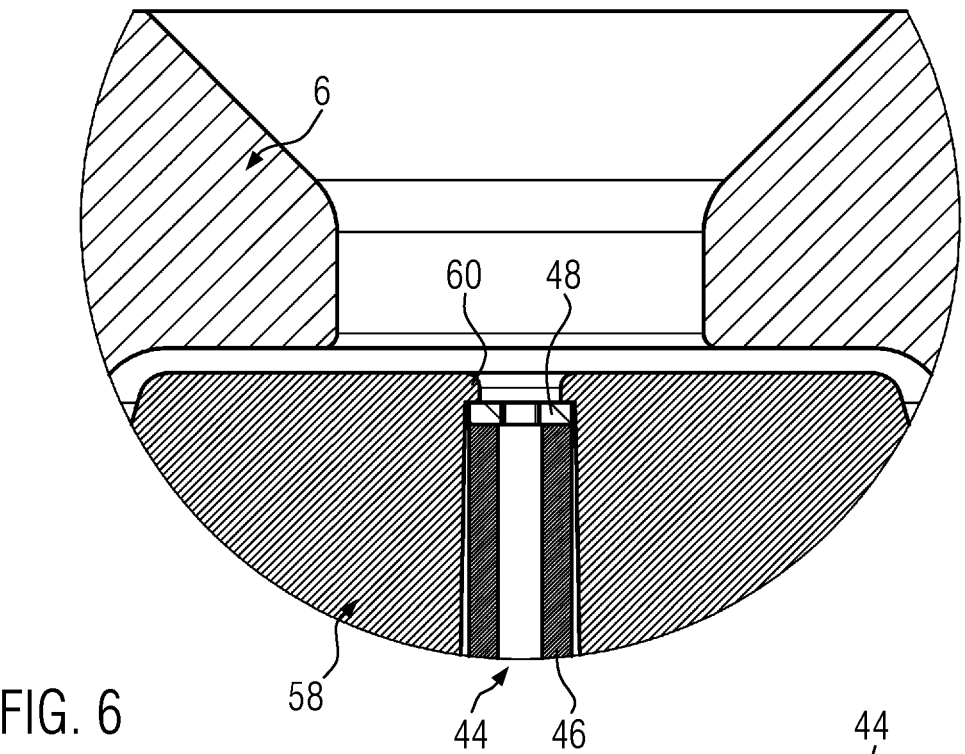
FIG. 6 shows detail VI according to FIG. 4.

The end of the nozzle element 44 on the outlet side is received in a nozzle cap 58 which forms a flange region 60, as illustrated in FIG. 6, which reaches over the nozzle element 44 on the face side and abuts against the aperture plate 48 at the face side, and accordingly provides a positive-fit lock of the nozzle element 44 which prevents the nozzle element 44 from exiting in the axial direction from the nozzle holder 32 due to the liquid pressure acting thereupon.

The nozzle cap 58 forms a substantially cylindrical receptacle 62 for the end of the nozzle holder 32 on the outlet side. This receptacle 62 radially surrounds the nozzle holder 32.

The nozzle cap 58 on the end at the face side of this receptacle 62 comprises a ring-shaped groove 64 which is adapted to receive the ring-shaped rim 54 and is defined radially in the interior by a centering collar 66 which projects into the ring-shaped free space 56.

The nozzle cap 58 has a radially extending adhesive introduction opening 68 which is provided in the axial direction approximately at the level of the ring-shaped free space 56. This adhesive introduction opening in turn has an axial spacing from the end of the nozzle holder 32 on the outlet side formed, firstly, by the ring-shaped rim 54 and, secondly, by an end of the nozzle cap 58 on the inlet side. A small clearance is provided between the nozzle cap 58 and the nozzle holder 32, so that the adhesive introduced through the adhesive introduction opening 68 can spread both in the region of the receptacle 62 between the inner circumferential surface of the nozzle cap 58 and the nozzle holder 62 as well as on the face side between the nozzle holder 32 and the nozzle cap 58. Any excess adhesive can enter the free space 56 without it needing to be feared that the adhesive will block the nozzle element 44 on the outlet side. The free space 56 is accordingly designed as a reservoir for receiving excess adhesive.

As illustrated by FIGS. 3 and 4, the casing cap 6 has an abutment shoulder 70 against which the adapter element 20 abuts on the face side, whereby the adapter element 20, and thus the nozzle holder 32 adhesively bonded thereto, are axially fixed to the nozzle cap 58 bonded thereto.

Figure 7:
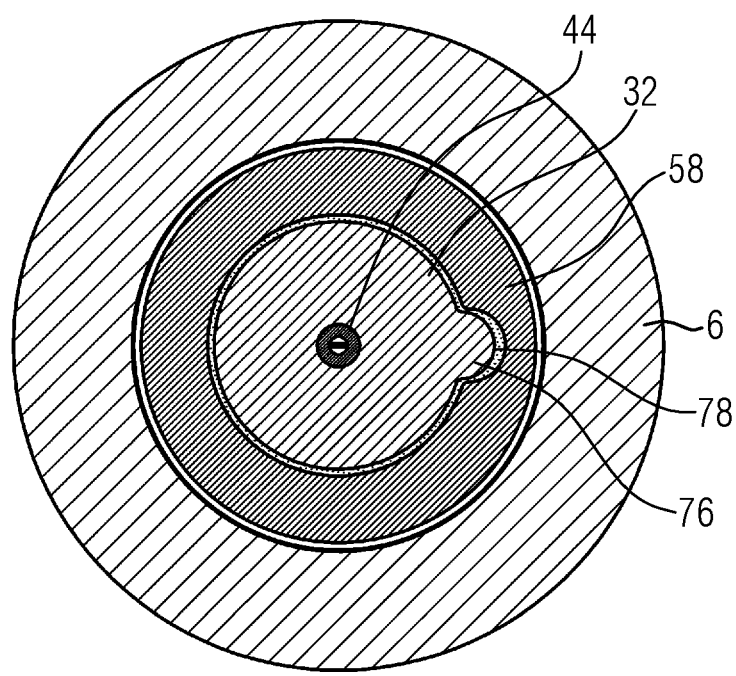
FIG. 7 shows a sectional view along the line VII-VII according to FIG. 4.
Figure 9:
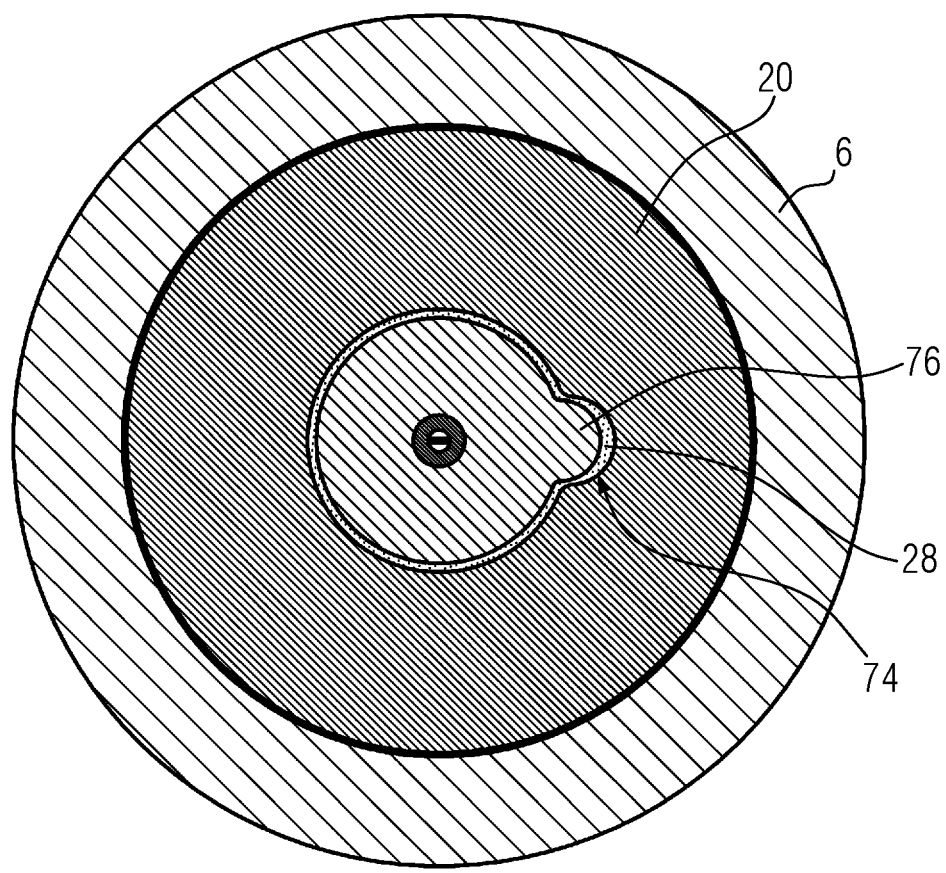
FIG. 9 shows a sectional view along the line IX-IX according to FIG. 4.

When producing the embodiment, the transparent plastic material forming the nozzle holder 32 is first injected into an injection mold into which the nozzle element 44 projects on the inlet side. A die forming the flow channel 40 sealingly abuts against the nozzle element 44 at the end side, so that no plastic material can there enter the nozzle element 44. The unit of the nozzle holder 32 and the nozzle element 44 thus produced is demolded. The nozzle cap 58, which is also first produced separately by way of injection molding, is then pushed over the end of the nozzle element 44 on the outlet side. UV-curable one component adhesive is introduced through the adhesive introduction opening 68 and spreads between the nozzle holder 32 and the nozzle cap 58 and is cured by UV radiation. In this manner, a separately manipulatable subunit in the form of a nozzle element holder 72 is provided. This nozzle element holder 72 has positive-fitting features for radial positioning of the nozzle holder 32 in the adapter element 20, which are illustrated in FIGS. 3 and 4, respectively, in a perspective longitudinal sectional view and in a longitudinal sectional view, respectively, and in cross-section in FIGS. 7 and 9. On its opening on the outlet side which leads to the nozzle holder receptacle 30, the adapter element 20 has an axially extending positioning groove 74 into which a positioning rib 76 extends that projects over the substantially cylindrical outer circumferential surface of the nozzle holder 32 (FIG. 9). The positioning rib 76 is extended in the axial direction into the nozzle cap 58 and there engages in a positioning groove indicated by reference numeral 78 in FIG. 7, which is recessed on the inner circumference on the nozzle cap 58.

Radial positioning of the nozzle cap 58 relative to the nozzle holder 32 and radial positioning of the nozzle holder 32 and thus of the preassembled nozzle element holder 72 relative to the adapter element 20 is predetermined by this configuration.

Figure 8:
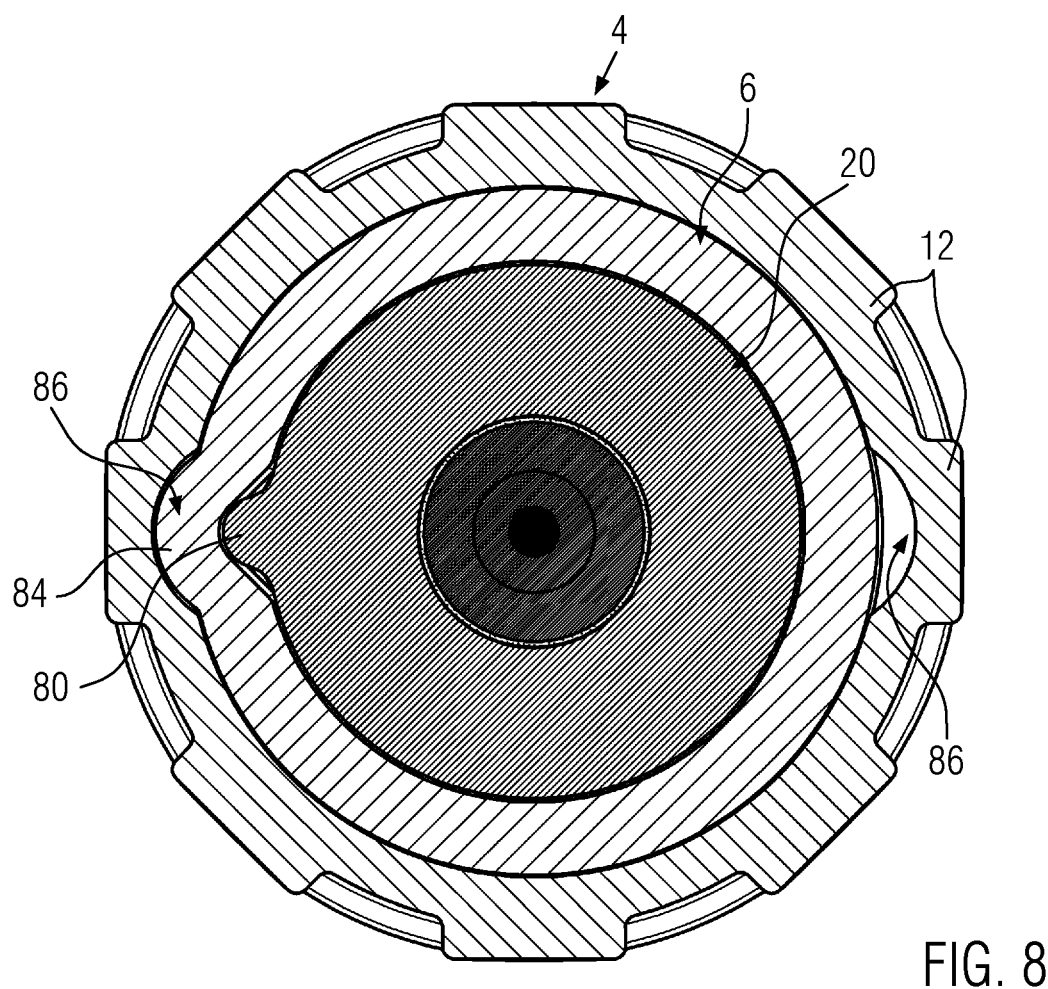
FIG. 8 shows a sectional view along the line VIII-VIII according to FIG. 4.

As illustrated in FIG. 8, the adapter element 20 has a corresponding configuration on its outer circumferential surface for radial positioning in the form of a positioning rib 80 which is provided as a positive-fit element on the adapter element 20 and which engages in a positioning groove 82 which is recessed on the casing cap 6. At this position, a further positioning rib 84 protrudes from the outer circumferential surface of the casing cap 6 and engages in a further positioning groove 86 which is recessed on the inner circumferential surface of the handle shaft 4. The respective further development makes it possible to precisely position a nozzle element, which is configured with a wide jet nozzle shown in FIG. 7, relative to the handpiece casing 2. In order to simplify the assembly, the handle shaft 4 has two positioning grooves 86 offset at an angle of 180° which optionally interact with the positioning rib 84 without distorting the desired orientation of the wide jet nozzle relative to a position indicator which can be provided on the handpiece casing 2.

Figure 10:
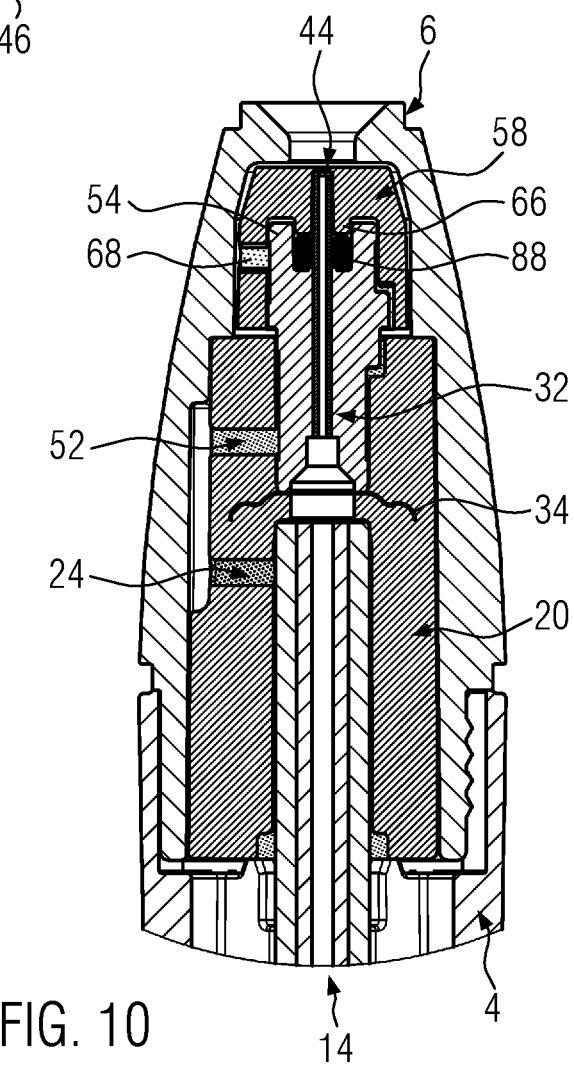
FIG. 10 shows a variant as a second embodiment which is slightly modified as compared to the above-described first embodiment.

FIG. 10 shows a sectional view according to FIG. 4 for an alternative embodiment. Identical components are marked with the same reference symbols. This alternative embodiment differs from the previously discussed embodiment by an O-ring 88 which is inserted into the free space 56 and is clamped between the centering collar 66 and a ring-shaped arc of the free space 56 in order to sealingly abut, firstly, against the outer circumferential surface of the nozzle element 44 penetrating this O-ring 88 and, secondly, against the inner circumference surface of the ring-shaped rim 54. This O-ring provides a safety measure in the event that the circumferential sealing of the nozzle element 44 via the nozzle holder 32 is damaged during operation.

LIST OF REFERENCE NUMERALS 2 handpiece casing
4 handle shaft
6 casing cap
8 positive-fit connection
10 attachment nose
12 rib
14 tube
16 inner tube section
18 outer tube section
20 adapter element
22 tube well
23 annular shoulder
24 adhesive introduction opening
26 annular space
28 adhesive
30 nozzle holder receptacle
32 nozzle holder
34 filter element
36 annular shoulder
38 flow channel
40 flow channel
42 cylindrical channel section if the flow channel 40
44 nozzle element
46 pipe member
48 aperture plate
50 groove
52 adhesive introduction opening
54 ring-shaped rim
56 free space
58 nozzle cap
60 flange region
62 receptacle
64 ring-shaped groove
66 centering collar
68 adhesive introduction opening
70 abutment shoulder
72 nozzle element holder
74 positioning groove of the adapter element 20
76 positioning rib of the nozzle holder 32
78 positioning groove of the nozzle cap 58
80 positioning rib of the adapter element 20
82 positioning groove of the casing cap 6
84 positioning rib of the casing cap 6
86 positioning groove of the handle shaft 4
88 O-ring

What is claimed:

1. A handpiece for spraying a fluid jet with a handpiece casing in which a nozzle element for forming a jet geometry of the fluid jet is accommodated, the handpiece comprising the handpiece casing and the nozzle element, and further comprising an adapter element comprising a nozzle holder receptacle adapted to receive a nozzle holder and a tube well that receives a tube for supply of fluid forming the fluid jet that is in communication with said nozzle element; wherein said nozzle element is fixedly connected to said nozzle holder which sealingly abuts against an outer circumferential surface of said nozzle element and is fixed relative to said handpiece casing; wherein a filter element is arranged between said nozzle holder and said tube; wherein said nozzle holder and said tube are adhesively bonded to said adapter element; and wherein said adapter element comprises an adhesive introduction opening radially reaching up to said nozzle holder and an adhesive introduction opening radially reaching up to said tube.

2. The handpiece according to claim 1, wherein an outlet end of said nozzle element projects over said nozzle holder, and wherein an inlet end of said nozzle element is received within said nozzle holder.

3. The handpiece according to claim 1, wherein said nozzle holder is formed from plastic material and is connected to said nozzle element by way of overmolding.

4. The handpiece according to claim 3, wherein an outer circumferential surface of said nozzle element comprises at least one radially extending groove for a positive-fit connection between said nozzle holder and said nozzle element.

5. The handpiece according to claim 1, wherein a flow channel is formed in said nozzle holder, a diameter of said flow channel is greater than an outer diameter of said nozzle element, and said flow channel is disposed upstream of an inlet end of said nozzle element.

6. The handpiece according to claim 1, further comprising a nozzle cap which reaches over said nozzle holder and receives an outlet end of said nozzle element, which outlet end projects over said nozzle holder.

7. The handpiece according to claim 6, wherein a free space is formed between said nozzle holder and said nozzle cap, which free space is penetrated by said nozzle element, and wherein said outlet end of said nozzle element projecting over said nozzle holder and is received within the nozzle cap.

8. The handpiece according to claim 6, further comprising an O-ring which is provided between said nozzle cap and said nozzle holder and penetrated by said nozzle element.

9. The handpiece according to claim 1, wherein said nozzle holder and said tube are connected by overmolding to said adapter element.

10. A handpiece for spraying a fluid jet with a handpiece casing in which a nozzle element for forming a jet geometry of the fluid jet is accommodated, the handpiece comprising the handpiece casing and the nozzle element, and further comprising an adapter element comprising a nozzle holder receptacle adapted to receive a nozzle holder and a tube well that receives a tube for supply of fluid forming the fluid jet that is in communication with said nozzle element; wherein said nozzle element is fixedly connected to said nozzle holder which sealingly abuts against an outer circumferential surface of said nozzle element and is fixed relative to said handpiece casing; and wherein an outer circumferential surface of said adapter element is provided with a projecting rib forming a positive-fit element which interacts with a positive-fit mating element in the form of a radial groove recessed in a casing cap, said casing cap radially reaches over a nozzle cap, said nozzle cap provides a receptacle radially surrounding the nozzle holder, wherein the nozzle cap is adhesively bonded to said nozzle holder.

11. A handpiece for spraying a fluid jet with a handpiece casing in which a nozzle element for forming a jet geometry of the fluid jet is accommodated, the handpiece comprising the handpiece casing and the nozzle element, and further comprising an adapter element comprising a nozzle holder receptacle adapted to receive said nozzle holder and a tube well that receives a tube for supply of fluid forming the fluid jet that is in communication with said nozzle element wherein said nozzle element is fixedly connected to said nozzle holder which sealingly abuts against an outer circumferential surface of said nozzle element and is fixed relative to said handpiece casing; wherein a filter element is arranged between said nozzle holder and said tube; and further comprising a nozzle cap, which reaches over said nozzle holder on the outlet side, wherein said nozzle cap is formed of a transparent plastic material and is adhesively bonded to said nozzle holder, wherein an adhesive introduction opening radially extends in said nozzle cap to reach up to the nozzle holder, wherein a free space is formed between said nozzle holder and said nozzle cap, which free space is penetrated by said nozzle element, wherein an outlet end of said nozzle element projects over said nozzle holder and is received within the nozzle cap.

12. The handpiece according to claim 11, wherein said nozzle cap radially reaches over said nozzle element.

13. The handpiece according to claim 1, wherein said nozzle holder is integrally formed.

14. The handpiece according to claim 10, wherein said nozzle holder is integrally formed.

\* \* \* \* \*